United States Patent [19]

Melillo et al.

[11] Patent Number: 4,758,661

[45] Date of Patent: Jul. 19, 1988

[54] CHIRAL SYNTHESIS OF (+)-TRANS-1A,2,3,4A,5,6-HEXAHYDRO-9-HYDROXY-4-PROPYL-4H-NAPHTH[1,2-B]-1,4-OXAZINE

[75] Inventors: David G. Melillo, Scotch Plains; David J. Mathre, Edison; Robert D. Larsen, Monmouth Junction, all of N.J.

[73] Assignee: Merck & Co., Inc., Rahway, N.J.

[21] Appl. No.: 877,816

[22] Filed: Jun. 24, 1986

[51] Int. Cl.$^4$ .......................................... C07D 265/34
[52] U.S. Cl. ................................. 544/101; 549/243; 560/28; 560/29; 560/159; 564/428
[58] Field of Search ....................... 544/101; 564/428; 560/28, 29, 159; 549/243

[56] References Cited

U.S. PATENT DOCUMENTS 4,420,480  12/1983  Jones et al. ..................... 544/101 X

OTHER PUBLICATIONS

J. Org. Chem., 50, 3619, (1985), Nordlander et al.
J. Org. Chem., 46, 2431, (1981), McClure et al.
J. Org. Chem., 48, 2675, (1983), McClure et al.
J. Med. Chem., 27, 1607, (1984), Jones et al.
Eur. J. Med. Chem. Chim. Ther, 20,(3), 247–250, (1985).

*Primary Examiner*—Richard L. Raymond
*Attorney, Agent, or Firm*—William H. Nicholson; Michael C. Sudol

[57] ABSTRACT

(+)-trans-1a,2,3,4a,5,6-Hexahydro-9-hydroxy-4-propyl-4H-naphth[1,2-b]-1,4-oxazine is elaborated by a series of process steps that retain the enantiomeric purity of the starting material, D-aspartic acid. The product is a direct acting dopaminergic agent, useful in the treatment of Parkinson's disease.

1 Claim, No Drawings

CHIRAL SYNTHESIS OF (+)-TRANS-1A,2,3,4A,5,6-HEXAHYDRO-9-HYDROXY-4-PROPYL-4H-NAPHTH[1,2-B]-1,4-OXAZINE

SUMMARY OF THE INVENTION

This invention is concerned with a novel process for the chiral synthesis of (+)-trans-1a,2,3,4a,5,6-hexahydro-9-hydroxy-4-propyl-4H-naphth-[1,2-b]-1,4-oxazine, known hereinafter as noxazinol, with chemical structure:

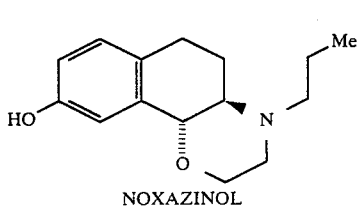

NOXAZINOL useful in the treatment of Parkinson's disease.

This invention is also concerned with a novel intermediate compound in the process and a novel process for preparing the intermediate of chemical structure:

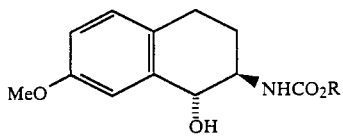

The overall process is summarized by the following Reaction Scheme I:

REACTION SCHEME I

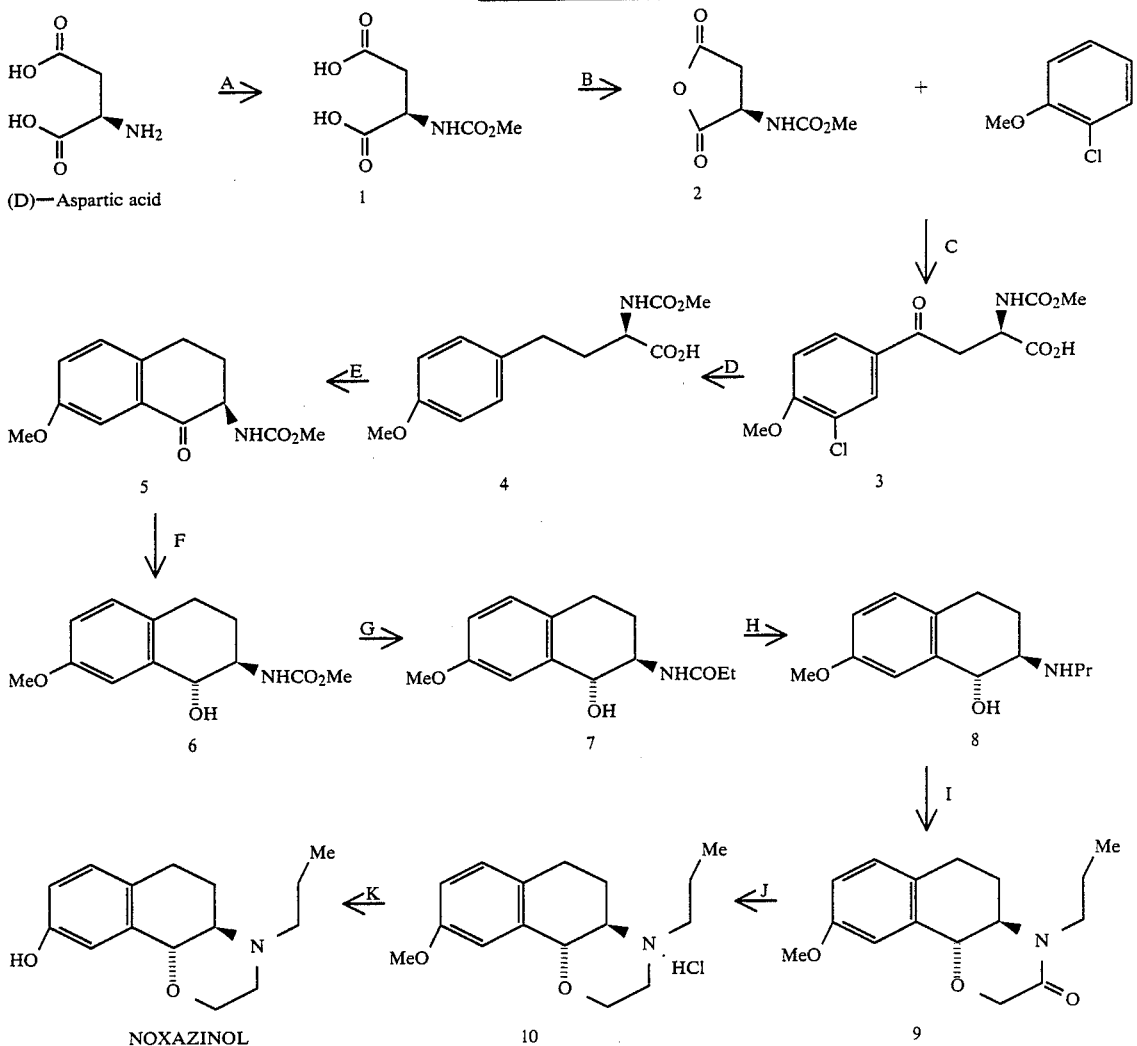

BACKGROUND OF THE INVENTION

Noxazinol is described in U.S. Pat. No. 4,420,480 by Jones along with a process for its preparation. This prior art process requires several steps but most importantly results in a racemic product which must be resolved to obtain the desired enantiomers which results in the loss of at least 50% of synthetic product.

Similarly with Dykstra et al., *Eur. J. Med., Chim. Ther.* 247–250 (1985); and Jones et al, *J. Med. Chem.*. 27. 1607–1613 (1984), the final product or intermediate must be resolved resulting in loss of synthetic material.

Chemistry similar to some of the steps in the novel process of this invention have been described in the literature. For example McClure et al., *J. Org. Chem.* 46, 2431-2433 (1981) describes a Friedel-Crafts ring closure similar to the step 4→5 in Reaction Scheme I but involves formation of a 5-membered ring fused to an unsubstituted benzo group. Also McClure et al *J. Org. Chem.*. 48, 2675-2679 (1983) describes the same ring closure to form a 6-membered ring fused to an unsubstituted benzo group. It further describes a failure to ring close to a 5-membered fused ring wherein the benzo group carried a methoxy meta to the point of closure. This suggests the claimed step 4→5 would not work.

Now with the present invention there is provided a novel process which starts with a simple chiral synthon, D-aspartic acid, from which noxazinol is elaborated in a sequence of steps each of which proceeds in high yield and retention of enantiomeric purity.

DETAILED DESCRIPTION OF THE INVENTION

The novel process of this invention is described below wherein each process step relates to the step of the Example that follows and each intermediate is as identified in Reaction Scheme I.

Step A:

D-Aspartic acid and a slight excess of sodium or potassium hydroxide (about 4 moles/mole of D-aspartic acid) in water at about $-5°$ to $+80°$ C. is treated with a slight excess of a $C_{1-3}$ alkyl haloformate, preferably methyl or ethyl chloroformate over a period of about 20 to 60 minutes followed by stirring for about 0.5 to 2 hours or longer. Acidification provides the free diacid 1 which can be isolated by extraction with an organic solvent.

Step B:

The diacid 1 in an inert organic solvent such as a lower alkyl acetate, e.g. ethyl or isopropyl acetate or a halogenated alkane such as chloroform, methylene chloride, 1,2-dichloroethane or the like is treated with (1) a slight excess of oxalyl chloride and a catalytic amount of DMF; (2) ketene; (3) a slight excess of trifluoroacetic acid. Procedure (3) is preferred, in part because crystalline material is isolated directly. After 1 to 4 hours the anhydride product 2 is obtained by evaporation and recrystallization.

Step C:

The anhydride is added at about $-5°$ C. to reflux temperature to a Friedel-Crafts catalyst such as $AlCl_3$ in nitromethane/methylene chloride and 2-chloroanisole with a nitrogen sweep to remove HCl gas as it is formed. After stirring for about 1 to 5 days the reaction is quenched by addition to a cold mixture of methylene chloride, isopropyl acetate, or ethyl acetate and aqueous phosphoric acid. Alternatively the $AlCl_3$/nitromethane/methylene chloride solution is added to a refluxing suspension of 2-chloroanisole and the anhydride in methylene chloride. Reaction is complete in about 0.5 to 2 days. The Friedel-Crafts product, 3, is isolated by extraction procedures.

Step D:

The chloro ketone, 3, is reduced with hydrogen and a noble metal catalyst such as platinum, Raney nickel, or palladium on carbon, preferably the latter in aqueous acetic acid, aqueous THF, ethyl acetate or isopropyl acetate and optionally in the presence of sodium acetate at about 10-1000 psi of hydrogen for about 10 to 48 hours to produce the amino acid 4 by reduction of the carbonyl and hydrogenolysis of the chloro group from the phenyl moiety.

Step E:

The amino acid, 4, is converted to the acid chloride with a chlorinating agent such as oxalyl chloride/DMF, phosgene/DMF, or $PCl_5$ and then added slowly at about $-5°$ C. to reflux temperature to a Friedel-Crafts catalyst such as $FeCl_3$ in methylene chloride/nitromethane or nitrobenzene, $AlCl_3$, $AlCl_3$ with nitromethane, $SnCl_4$ or $TiCl_4$. After about 0.5 to 3 hours the reaction is quenched with phosphoric acid and the tetralone product, 5, is isolated.

Step F:

The tetralone, 5, is reduced by addition of it to sodium bis(methoxyethoxy)aluminum hydride in an aromatic solvent such as benzene or toluene or an ethereal solvent such as diethyl ether, THF, or 1,2-dimethoxyethane at about $-75°$ to $+5°$ C., over a period of about 0.5 to 2 hours. After an additional 0.5 to 2 hours the excess hydride is quenched by addition of sulfuric acid or aqueous sodium potassium tartrate and the product is isolated. This stereospecific reduction results in a yield of about 85-90% of material that is greater than 99% transalcohol, 6.

The same product is obtained by reduction of the tetralone with sodium borohydride in ethanol but only in about 40% yield and much lower isomeric purity.

Step G:

The carbamate group of 6 is hydrolyzed by treatment with an excess of aqueous sodium or potassium hydroxide in aqueous methanol by heating at about $75°$-$100°$ C. for about 4 to 12 hours.

Alternatively, the carbamate is saponified in a mixture of toluene and 10% (w/v) aqueous sodium hydroxide in the presence of a phase transfer catalyst such as tetra (n-butyl)ammonium chloride at about $20°$-$110°$ C. for about 10 minutes to 8 hours.

After cooling to about $-5°$ C. to $+5°$ C. propionic anhydride is added slowly over about 2-6 hours to give the propionamide, 7, which is isolated in about 90-95% yield, after heating to about $70°$ C. for a short period.

Step H:

The propionamide, 7, is reduced with boranedimethylsulfide complex in an ethereal solvent such as THF, diethyl ether, 1,2-dimethoxyethane or the like at about $20°$-$30°$ C. during the addition of the complex over about 30 minutes to 1 hour followed by heating at about reflux temperature for about 1 to 2 hours. After cooling to about $0°$ C., the excess complex is destroyed by the addition of a mineral acid preferably a 1:1 (v/v) mixture of concentrated HCl and methanol and the propylamino compound, 8, is isolated in about 85-90% yield with about 99% enantiomeric purity.

Step I:

The amino function of the amino alcohol, 8, is acylated with a haloacetyl halide, preferably chloroacetyl chloride to form the N-haloacetyl derivative. The acylation is readily performed by slow addition of the acid halide to a solution of the amino alcohol in a mixture of an aromatic solvent such as benzene or toluene and an aqueous base, preferably sodium carbonate, at about $20°$ to $30°$ C. for about 0.25 hours to 1 hour after addition is complete.

The N-acetylated intermediate is cyclized to the oxazinone, 9, by the addition of aqueous sodium hydroxide and a phase transfer catalyst such as tetra-n-butylammonium chloride catalyst or Aliquot 336, and stirring for about 0.5 to 3 hours at about $20°$ to $30°$ C.

Step J:

The carbonyl function of the oxazinone, 9, is reduced to form the oxazine, 10. The reduction is readily accomplished with sodium bis(methoxyethoxy)aluminum hydride by the procedure described above, in Step F, or with lithium aluminum hydride in an ethereal solvent, or with diborane in an ethereal solvent.

Step K:

De-etherification of the oxazine, 10. to the final product can be accomplished by various procedures, such as with boron tribromide, methionine in methanesulfonic acid, or pyridine hydrochloride.

In the former the oxazine hydrochloride and cyclohexene in a chlorinated hydrocarbon such as chloroform, or methylene chloride is treated with boron tribromide for about 0.5 to 12 hours at about 20°–30° C. and the reaction is subsequently quenched by the addition of water.

In the methionine/methanesulfonic acid process the methyl ether, 10. is added slowly to a solution of methionine in methanesulfonic acid and stirred for about 36–48 hours at about 20° to 30° C. The cooled mixture is then diluted with water and made alkaline.

EXAMPLE

Step A:

A solution of D-aspartic acid (133.1 g, 1.0 mole) and sodium hydroxide (160 g, 4.0 moles) in 500 ml of water was cooled to $-5°$ C. and methyl chloroformate (147 g, 1.58 moles) was added dropwise over 30 minutes. The solution was stirred at $-5°$ to $+10°$ C. for 1 hour and then the pH was adjusted to 1 by dropwise addition of concentrated aqueous HCl. Using a continuous extraction apparatus, the product was extracted into isopropyl acetate. Evaporation of the solvent gave the pure diacid, 1, as a white solid (172 g, 90%), m.p. 152°–153° C.

Step B:

To a stirred solution of diacid, 1, (1.00 g, 5.23 mmole) in 40 ml isopropyl acetate at room temperature was added oxalyl chloride (0.80 g, 6.30 mmole) followed by dimethylformamide (35 mg, 0.53 mmole). The solution was stirred at room temperature for 2 hours and concentrated in vacuo. The solid residue was triturated with 50% hexane-ether. The filtered solid was dried to give 0.78 g (86%) of the anhydride, 2, as a pale yellow solid, m.p. 134°–138° C.

Step B Alternate:

Trifluoroacetic anhydride (25.3 g, 120 mmole) was added dropwise to a stirred suspension of the diacid, 1, (19.1 g, 100 mmole) in 260 ml isopropyl acetate at room temperature. The solution was aged for 2 hours and then diluted with 1.3 L hexane. The suspension was aged at room temperature for 1.5 hours, filtered, and the solid was washed with 15% isopropyl acetate/hexane. The white solid was vacuum-dried to 16.1 g (93%) of 2.

Step B Alternate:

Ketene gas, generated by pyrolysis of acetone vapors, was bubbled through a suspension of diacid, 1, (3.82 g, 20.0 mmole) in 50 ml isopropyl acetate at room temperature until the dehydration was complete—a homogeneous solution is a sign that the reaction is nearly done. The solution was concentrated to give 4.2 g of pale yellow solid. The crude product was stirred in 50% hexane-ether, filtered, and vacuum-dried to afford 3.26 g (94%) of the anhydride, 2, as a pink solid.

Step C:

To a solution of AlCl$_3$ (2.80 g, 21.0 mmol) in a mixture of 2.30 ml nitromethane and 20 ml anhydrous CH$_2$Cl$_2$ at 0° C. was added 2-chloroanisole (2.81 g, 19.7 mmole) followed by a suspension of the anhydride (1.73 g, 10.0 mmole) in a mixture of 2.3 ml nitromethane and 5 ml CH$_2$Cl$_2$. The resulting solution was stirred at room temperature for 5 days and then quenched by addition into an ice-cold mixture of 50 ml CH$_2$Cl$_2$ and 100 ml of 0.5M aqueous H$_3$PO$_4$. The layers were separated and the aqueous layer extracted with another 50 ml portion of CH$_2$Cl$_2$. The combined organic layers were washed with 50 ml of 1M aqueous H$_3$PO$_4$ and then the product was extracted into three 35 ml portions of 1M aqueous NaHCO$_3$. The combined aqueous extracts were washed with 50 ml CH$_2$Cl$_2$ then the pH was adjusted to 1 by addition of concentrated aqueous HCl. The product was extracted into three 50 ml portions of CH$_2$Cl$_2$. The combined organic layers were washed with brine, dried over MgSO$_4$, and concentrated to give the product, 3, as 3.00 g (95%) of a pale yellow foamy solid, m.p. 152°–153° C.

Step D:

A suspension of the chloroketone, 3, (1.17 g, 3.7 mmole), sodium acetate (0.50 g, 6.1 mmole) and 0.50 g of 10% Pd/C in 25 ml of 5% aqueous HOAc was shaken at room temperature under 40 psi H$_2$ for 18 hours. The vented suspension was filtered and the solution was concentrated in vacuo to near dryness. The residue was dissolved in ethyl acetate and washed with 1N aqueous HCl followed by H$_2$O. The organic layer was dried over MgSO$_4$, filtered and concentrated to give 0.91 g (92%) of the acid, 4, as a tan solid, m.p. 113°–114° C.

Step E:

To a stirred suspension of the acid, 4, (408.7 g, 1.53 mol) in 1.5 L of CH$_2$Cl$_2$ at 0° C. was added oxalyl chloride (198.0 g, 1.56 mol) followed by 6.0 ml of dimethylformamide catalyst. The resulting solution was allowed to warm to room temperature and aged for 2 hours and then added over a period of 1.5 hours to a cooled ($-5°$ C.) solution of FeCl$_3$ (744 g, 4.59 mol) in 22 L of CH$_2$Cl$_2$ and 745 ml CH$_3$NO$_2$. The reaction was aged for 1 hour and then quenched by addition of 12L of 1M aqueous H$_3$PO$_4$. After stirring for 1 hour, the layers were separated. The aqueous layer was extracted with another 2L CH$_2$Cl$_2$. The combined organic layers were washed with 8 L of 1M aqueous H$_3$PO$_4$ followed by 8 L of brine. Silica gel (2 kg) was added to the organic solution, filtered, and the cake thoroughly washed with CH$_2$Cl$_2$. The filtrate was concentrated to give 340 g (89%) of the tetralone, 5, as a slightly orange solid, m.p. 136°–137° C.

Step F:

To a solution of 675 ml of 3.4M (2.30 mole) Red-Al ® in toluene diluted with 6.7 L toluene and cooled to $-5°$ C. was added portionwise, as a solid, 331 g (1.33 mole) of tetralone, 5, over an hour. After aging at $-5°$ C. for 1 hour, the solution was quenched by cautious addition of 8 L of 3.6N aqueous H$_2$SO$_4$. Stirring was continued at 5°–10° for 1 hour and then the suspension was filtered. The product was washed with four 4 L portions of H$_2$O and then vacuum dried to give 392.7 g of white solid. This crude product, 6, by HPLC assay was 76% pure, the yield adjusted for purity was 89.5%. The impurities, which were inorganic aluminum salts, can be removed by washing a methylene chloride solution with aqueous NaOH. In this manner, pure carbamate (>99%) is prepared in 86% yield from the tetralone, m.p. 159°–160° C. Most importantly, the material is devoid of the cis-isomer.

Step F Alternate:

A suspension of the tetralone, 5, (66.5 g, 0.267 mole) in 1 L of 200 proof ethanol and 150 ml of tetrahydrofuran at 0°–5° C. was treated with sodium borohydride (12.6 g, 0.333 mole) as a solid. The mixture was stirred for 3 hours and then quenched by cautious addition of 50 ml acetic acid. After addition of 200 ml H$_2$O, the mixture was concentrated in vacuo to an oily solid which was diluted with 400 ml 2N aqueous HCl and extracted with three portions (total volume 500 ml) CH$_2$Cl$_2$. The organic extracts were dried over MgSO$_4$, filtered, and concentrated to give 78.6 g of crude product, 6, as a tan solid. To remove several impurities, including 14% of the cis-isomer, the crude product was stirred in 700 ml diethyl ether at room temperature overnight. The product was filtered, washed with several portions of ether and vacuum-dried to give 26.85 g (40%) of the trans-alcohol, 6, as a tan solid.

Step G:

To a mechanically stirred suspension of the carbamate, 6, (237 g, 0.943 mole) in 2.4 L of methanol was added a solution of 378 g (9.44 mole) NaOH in 480 ml H$_2$O. The suspension was heated at reflux for 9 hours. The suspension was cooled to 0° and then 850 ml propionic anhydride was added slowly over 4 hours. The mixture was diluted with 12 L of water containing 2 kg NaCl and filtered. The solid product was washed with two 2 L portions of H$_2$O and dried in vacuo to give 215.2 g of a white solid. An additional 22.1 g of product was obtained from the filtrate by salting with 2.5 kg NaCl and extracting with 3×2 L CH$_2$Cl$_2$. The total yield of hydroxy amide, 7, was 237.3 g or 217.6 g (93%) based on HPLC purity, m.p. 166°–167° C.

Step H:

To a solution of the hydroxy amide, 7, (100 g, 0.40 mole) in 2 L anhydrous tetrahydrofuran at room temperature was added 105 g (1.38 mole) of borane dimethyl sulfide complex over 30 minutes. The reaction was heated to reflux for 1 hour, cooled to 0° C., and quenched cautiously by addition of a mixture of 300 ml concentrated aqueous HCl and 300 ml MeOH. After addition of 500 ml H$_2$O, the solution was aged at room temperature for 2 hours and then partially concentrated under reduced pressure. The residue was partitioned between 2 L H$_2$O and 1 L ethyl acetate. The aqueous layer was washed with another portion of ethyl acetate (500 ml). The combined organic layers were extracted with 500 ml of 5% aqueous HCl. The combined aqueous layers were basified (25% aqueous NaOH) with cooling and the product was extracted with 3×1 L CH$_2$Cl$_2$. The combined organic layers were dried (Na$_2$SO$_4$), filtered, and concentrated to give 81.2 g (86%) of the amino alcohol, 8, as a white solid. The enantiomeric purity of the product was checked by converting a sample to the N-benzoyl derivative (PhCOCl, NEt$_3$, CH$_2$Cl$_2$) and assaying on a Pirkle covalent (D-glycine) HPLC column [hexane:CH$_2$Cl$_2$:IPA, 70:28:2]. Only a trace (<1%) of the undesired S,S-isomer was detected.

The amino alcohol, 8, was recrystallized as follows: 76.5 g of crude was heated into 765 ml CH$_3$CN. The solution was cooled at room temperature overnight, then cooled to 0° for 2 hours. The solid was collected by filtration, washed with CH$_3$CN and vacuum dried to give 71.7 g (94%) of white needles, m.p. 131°–132.5° C.

Step I:

The amino alcohol, 8, (145.9 g, 0.621 mole) was dissolved in a mixture of toluene (2 L) and saturated aqueous sodium carbonate (365 g in 1459 ml H$_2$O) in a 5-L 3-necked flask fitted with a mechanical stirrer, addition funnel, thermometer, and nitrogen inlet. Chloroacetyl chloride (91.1 g, 0.807 mole) was added dropwise at room temperature over a 15 minute period. The reaction was stirred for 30 minutes.

NOTE: The entire reaction sequence can be followed by HPLC on a 4.6 mm×26 cm Zorbax C-8 column, eluant CH$_3$CN-H$_2$O-H$_3$PO$_4$ (60:40:0.1), 1.0 ml/minute, 230 nm. Retention times: amino alcohol 6.45 minutes, α-chloroacetamide 5.25 minutes, oxazinone 6.18 minutes, and oxazine 8.25 minutes.

The reaction mixture was treated with 10% aqueous sodium hydroxide (1459 ml) and tetra-n-butylammonium chloride catalyst (3.65 g) and the two-phase reaction was stirred at room temperature for 1.5 hours. The layers were separated and the aqueous layer was back-extracted with 580 ml toluene. The combined organic layers were washed with water (580 ml), aqueous HCl (580 ml), water (580 ml) and finally saturated sodium chloride (580 ml). The toluene layer was dried over sodium sulfate (200 g), filtered, and the filtrate containing oxazinone, 9, was used in the next step.

Step J:

Into a 5-L 3-necked flask fitted with a mechanical stirrer, addition funnel, thermometer, and nitrogen inlet tube was charged 274 ml of a 3.4M (0.932 mol) solution of Red-Al® in toluene followed by 440 ml toluene The solution was cooled to 5° C. and the toluene solution of the oxazinone, 9, from Step I was added dropwise over 1 hour keeping the reaction temperature below 10°. After the addition was complete, the ice-bath was removed and the reaction mixture was heated to 80° C. for 1 hour. The solution was cooled to room temperature and cautiously quenched by addition of 1.5 L of 5% aqueous NaOH. To aid in the hydrolysis of the aluminum salts, 8.6 g of tetra-n-butylammonium chloride was added and the mixture was stirred at room temperature for 3 hours. The layers were separated and the toluene layer was washed with two 1-L portions of 5% aqueous NaOH. The combined aqueous layers were back-extracted with 1 L toluene. The combined toluene layers were washed with water (3×1 L), then saturated sodium chloride (1 L), and dried over sodium sulfate. The toluene was removed in vacuo leaving the oxazine, 10, free base as a tan oil (163.7 g). The oil was dissolved in a mixture of ethanol:ethyl ether (1:9, 2429 ml) and transferred to a 5 L, 3-necked flask fitted with a mechanical stirrer. The oxazine hydrochloride, 10, was precipitated by addition of 7N ethanolic HCl (105 ml, 1.3 equivalents) with stirring at room temperature. After stirring for 1 hour at that temperature, the suspension was cooled in an ice-bath for 1 hour. The hydrochloride was collected by filtration and washed with cold ethanol:ether (1:9, 1 L) followed by ether (1 L). The product was vacuum-dried to provide 173.6 g (94% overall yield from the amino alcohol) of the oxazine hydrochloride, 10, as a white solid: m.p. 230°–232° C. $[\alpha]_D^{25} = +50.4°$ (c=0.1, EtOH).

Step K:

(Boron Tribromide Method)

A suspension of the oxazine hydrochloride, 10, (1.0 g, 3.36 mmol) and cyclohexene (0.28 g, 3.36 mmol) in 50 ml methylene chloride under nitrogen at room temperature was treated dropwise over 20 minutes with boron tribromide (1.01 g, 4.0 mmol). The reaction mixture was stirred for 1 hour and then quenched by addition of 10 ml H$_2$O. Methylene chloride was added to dissolve the precipitated solid and then the pH of the aqueous layer was adjusted to 9 with aqueous NH$_4$OH. The layers were separated and the aqueous layer was extracted with another two portions of CH₂Cl₂. The combined organic layers were concentrated to give the free base of Noxazinol as a yellow solid, 0.90 g which is 87 weight % pure by HPLC. The yield adjusted for purity is 94%. This free base can be converted to the hydrochloride as described below.

(Methionine Method)

A mixture of methionine (7.52 g, 50.44 mmol) in 50 ml methanesulfonic acid was prepared in a 250 ml 3-necked flask fitted with a mechanical stirrer and a nitrogen inlet tube. After stirring for 30 minutes at room temperature, the methoxy compound (5.0 g, 16.8 mmol) was added portionwise over a few minutes. The solution was stirred under a nitrogen atmosphere for 40 hours. The reaction mixture was cooled to 5°–10° C. and water (50 ml) was added at such a rate to keep the temperature below 15° C. The solution was adjusted to pH 13.5 with 20% aqueous NaOH (approximately 120 ml). Darco KB decolorizing carbon (1 g) was added and the mixture was stirred for 1.5 hours. The mixture was filtered through a pad of Super-Cel and the cake washed with water. The filtrate was adjusted to pH 9 with concentrated aqueous HCl. The suspension was cooled to 0°–5° C., aged for 1 hour, and the free base of noxazinal was collected by filtration, washed with water and vacuum-dried to give 3.85 g (93%) of a white solid.

The hydrochloride was prepared as follows. The free base was dissolved in 40 ml of warm (40° C.) ethanol. A 7N solution of HCl in ethanol (3 ml, 1.3 equivalents) was added to the solution of free base. Ethyl ether (40 ml) was then added to the suspension and the mixture was aged at room temperature for 1 hour then at 0°–5° for 1 hour. The solid was filtered, washed with 50% ethanol/ether then with Et₂O, and dried under vacuum to give 4.3 g (90%) of the hydrochloride salt as a white solid, m.p. 303°–305° C.

What is claimed is:

1. A process for the preparation of the compound of formula:

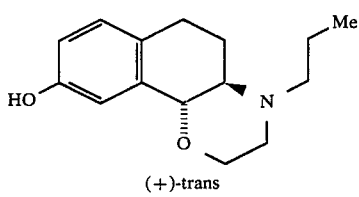

(+)-trans which comprises the steps of:
(a) treatment of D-aspartic acid with a lower alkyl haloformate to yield compound 1

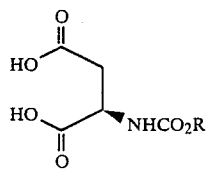

wherein R is C₁₋₃ alkyl;
(b) treatment of 1 with oxalyl chloride, trifluroacetic anhydride or ketene to yield compound 2

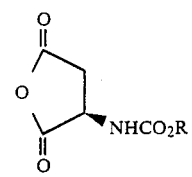

(c) treatment of 2 with 2-chloroanisole in the presence of a Friedel-Crafts catalyst to yield 3

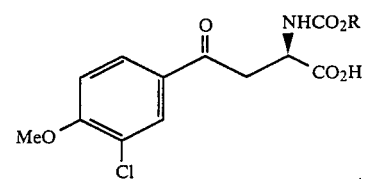

(d) treatment of 3 with hydrogen in the presence of a noble metal catalyst to yield 4;

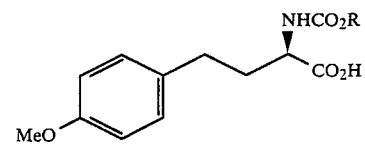

(e) treatment of 4 with a Friedel-Crafts catalyst to yield 5;

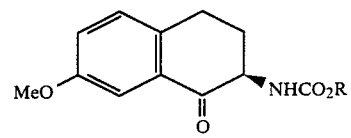

(f) treatment of 5 with a reducing agent by slow addition of 5 to a solution of sodium bis(methoxyethoxy) aluminum hydride in an aromatic solvent at −5° to +5° C. to yield 6;

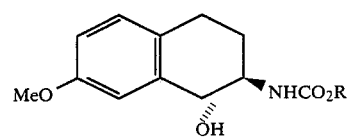

(g) treatment of 6 with alkali to remove the N-alkoxycarbonyl group followed by propanoylation to yield 7;

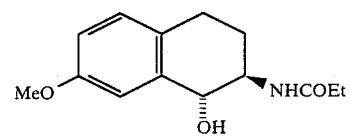

(h) treatment of 7 with a reducing agent to yield 8;

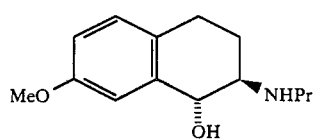
(i) treatment of 8 with a haloacetyl halide and a weak base followed by treatment with a strong base to produce 9;
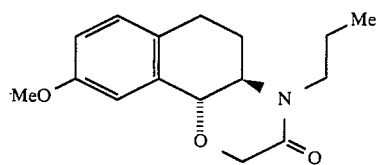
(j) treatment of 9 with a reducing agent to yield 10;
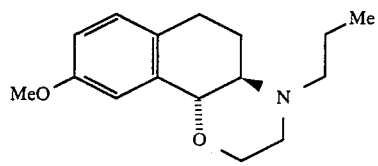
(k) treatment of 10 with boron tribromide or methionine methanesulfonate to yield 1.
* * * * *